United States Patent [19]

Ward et al.

[11] Patent Number: 4,818,754

[45] Date of Patent: Apr. 4, 1989

[54] CERTAIN ANTI-INFLAMMATORY PYRAZOLO [4,3-B] PYRIDINE 7-AMINES

[75] Inventors: Robert W. Ward; Roger E. Markwell; Ian Hughes, all of Harlow, England

[73] Assignee: Beecham Group p.l.c. of Beecham House, Brentford, England

[21] Appl. No.: 39,540

[22] Filed: Apr. 16, 1987

[30] Foreign Application Priority Data

Apr. 17, 1986 [GB] United Kingdom ............... 8609421

[51] Int. Cl.$^4$ ................... A61K 31/435; C07D 471/04
[52] U.S. Cl. ..................... 514/210; 514/212; 514/218; 514/253; 514/256; 514/293; 514/303; 514/228.5; 514/234.2; 540/467; 540/470; 540/524; 540/544; 540/575; 546/82; 546/119; 546/120; 544/55; 544/61; 544/96; 544/127; 544/333; 544/362
[58] Field of Search .............. 546/82, 119, 120; 544/127, 55, 61, 96, 362, 333; 540/524, 467, 470, 575, 544; 514/212, 210, 218, 222, 234, 236, 237, 253, 293, 256, 303

[56] References Cited

U.S. PATENT DOCUMENTS 4,559,348 12/1985 Hurst et al. ............... 546/119
4,621,089 11/1986 Ward et al. II ............... 546/119
4,670,432 6/1987 Ward et al. ............... 546/119

FOREIGN PATENT DOCUMENTS 0193329 9/1986 United Kingdom .

Primary Examiner—Mary C. Lee
Assistant Examiner—Bernard I. Dentz
Attorney, Agent, or Firm—James F. Haley, Jr.; David K. Barr; Teresa L. Solomon

[57] ABSTRACT

A compound of the formula (1) or a salt or solvate thereof:

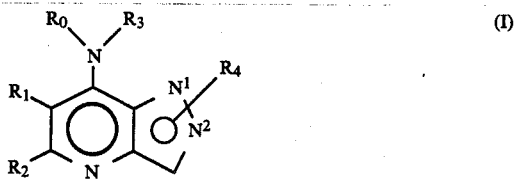

in which:

$R_0$ is hydrogen or $C_{1-6}$ alkyl;

$R_1$ and $R_2$ are both hydrogen; or $R_1$ is hydrogen, $C_{1-6}$ alkyl; and $R_2$ is CN; $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene; or $COR_{10}$ is OH or $C_{1-4}$ alkyl, or $COR_{10}$ is a pharmaceutically acceptable ester or amide; or $R_2$ is hydrogen, $C_{1-6}$ alkyl, or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above; or $R_1$ and $R_2$ together form $C_3$-$C_6$ polymethylene optionally substituted by $C_1$-$C_4$ alkyl;

$R_3$ is $-(CH_2)_nCO_2R_{11}$, $-(CH_2)_nCONR_{12}R_{13}$, $-(CH_2)_nCN$, $-(CH_2)_mNHCOR_{14}$, $-(CH_2)_m-O-\underset{\underset{O}{\|}}{C}-R_{14}$ $-(CH_2)_n-N(CH_2)_p$, or —

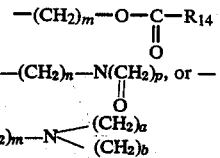

where a, b, n, m and p are integers and n is 1 to 10, m is 2 to 10, p is 3 to 5, a is 1 to 3, and b is 1 to 3, and $R_{11}$ is hydrogen, $C_{1-8}$ alkyl, benzyl or phenyl, $R_{12}$ and $R_{13}$ are independently hydrogen, $C_{1-6}$ alkyl, benzyl or phenyl, or together form $C_{3-8}$ alkylene, $R_{14}$ is $C_{1-4}$ alkyl, benzyl or phenyl and X is oxygen, sulphur, NH or N—$C_{1-4}$ alkyl, and $R_4$ is hydrogen; or $C_{1-4}$ alkyl or benzyl optionally substituted in the phenyl ring by one or two of halogen, $CF_3$, $C_{1-4}$ alkoxy or $C_{1-4}$ alkyl, and is attached at nitrogen atom 1 or 2, a process for its preparation and its use as a pharmaceutical.

9 Claims, No Drawings

CERTAIN ANTI-INFLAMMATORY PYRAZOLO [4,3-B] PYRIDINE 7-AMINES

The present invention relates to pyrazolopyridines having useful pharmacological activity, to a process for their preparation and to their use as anti-inflammatories.

EP-A-0152910 discloses compounds of the formula (A):

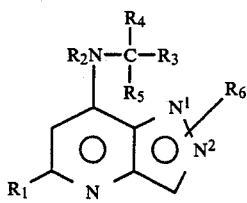

wherein:

$R_1$ is hydrogen, $C_{1-6}$ alkyl or phenyl optionally substituted by halogen, $CF_3$, $C_{1-4}$ alkoxy or $C_{1-4}$ alkyl;

$R_2$ is hydrogen or $C_{1-6}$ alkyl;

$R_3$ is $C_{2-10}$ alkenyl or $C_{1-10}$ alkyl substituted by hydroxy, $C_{1-4}$ alkoxy, thiol, $C_{1-4}$ alkylthio or $NR_7R_8$ wherein $R_7$ and $R_8$ are independently hydrogen or $C_{1-6}$ alkyl or together are $C_{3-6}$ polymethylene;

$R_4$ and $R_5$ are independently hydrogen or $C_{1-4}$ alkyl; and $R_6$ is hydrogen; or $C_{1-4}$ alkyl or benzyl attached at nitrogen atom 1 or 2.

These compounds are described as having anti-inflammatory properties.

A further group of pyrazolopyridine derivatives has now been discovered that has anti-inflammatory (including anti-rheumatic) and/or anti-allergy activity.

Accordingly, the present invention provides a compound of the formula (I) or a salt or solvate thereof:

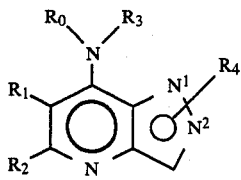

in which:

$R_0$ is hydrogen or $C_{1-6}$ alkyl;

$R_1$ and $R_2$ are both hydrogen; or $R_1$ is hydrogen, $C_{1-6}$ alkyl; and $R_2$ is CN; $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene; or $COR_{10}$ where $R_{10}$ is OH or $C_{1-4}$ alkyl, or $COR_{10}$ is a pharmaceutically acceptable ester or amide; or $R_2$ is hydrogen, $C_{1-6}$ alkyl, or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above; or $R_1$ and $R_2$ together form $C_3-C_6$ polymethylene optionally substituted by $C_1-C_4$ alkyl;

$R_3$ is —$(CH_2)_nCO_2R_{11}$, —$(CH_2)_nCONR_{12}R_{13}$, —$(CH_2)_nCN$, —$(CH_2)_mNHCOR_{14}$,

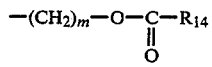

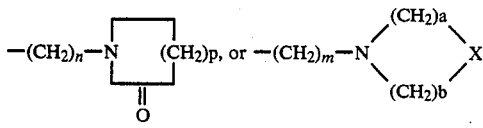

where a, b, n, m and p are integers and n is 1 to 10 m is 2 to 10, p is 3 to 5, a is 1 to 3, and b is 1 to 3, and $R_{11}$ is hydrogen, $C_{1-8}$ alkyl, benzyl or phenyl, $R_{12}$ and $R_{13}$ are independently hydrogen, $C_{1-6}$ alkyl, benzyl or phenyl, or together form $C_{3-8}$ alkylene, $R_{14}$ is $C_{1-4}$ alkyl, benzyl or phenyl and X is oxygen, sulphur, NH or N-$C_{1-4}$ alkyl, and $R_4$ is hydrogen; or $C_{1-4}$ alkyl or benzyl optionally substituted in the phenyl ring by one or two of halogen, $CF_3$, $C_{1-4}$ alkoxy or $C_{1-4}$ alkyl, and is attached at nitrogen atom 1 or 2.

Suitable values for $R_0$ include hydrogen, methyl, ethyl, n- and iso-propyl, preferably hydrogen.

Suitable values for $R_1/R_2$ include hydrogen, methyl, aminomethyl optionally N-substituted, and acetamidomethyl, or together forming $C_3$ or $C_4$ polymethylene.

Suitable values for $R_{10}$ when $R_1/R_2$ is $COR_{10}$ and $COR_{10}$ is a pharmaceutically acceptable ester or amide include $C_{1-6}$ alkoxy, $C_{2-6}$ alkenyloxy, phenoxy or benzyloxy where the phenyl/benzyl ring is optionally substituted by one or two of halogen, $CF_3$, $C_{1-4}$ alkoxy and $C_{1-4}$ alkyl; or $R_{10}$ is $NR_{20}R_{21}$ where $R_{20}$ and $R_{21}$ are independently hydrogen, $C_{1-6}$ alkyl, $C_{2-6}$ alkenyl, benzyl or phenyl optionally substituted as described above.

Suitable values for $R_3$ include 3-ethoxycarbonylpropyl, 3-(1-(2-oxopyrrolidinyl))propyl, 3-pentanoyloxypropyl, 2-(N-morpholino)ethyl, 3-acetoxypropyl, 2-benzoyloxyethyl, 3-benzylaminocarbonylpropyl, 2-pentanoyloxyethyl, 2-propionyloxyethyl, 3-(n-amlaminocarbonyl)propyl and 3-(iso-amyloxycarbonyl)propyl.

Suitable values for $R_4$ include hydrogen, methyl, ethyl, n- and iso-propyl and benzyl. More suitably $R_4$ is hydrogen or 2-methyl. Favourably $R_4$ is hydrogen. When $R_4$ is other than hydrogen it is preferably attached at nitrogen atom 2.

It will be appreciated that when $R_4$ is hydrogen the compounds of formula (I) exist as tautomers, i.e. the $R_4$ hydrogen atom is labile. The compounds wherein $R_4$ is hydrogen are therefore of formulae (IIa) and (IIb).

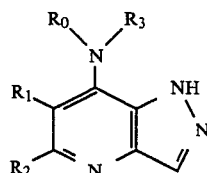

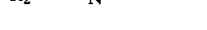

-continued

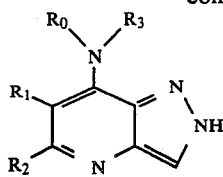
(IIb)

The compounds of the formula (I) can form acid addition salts with acids, such as the conventional pharmaceutically acceptable acids, for example hydrochloric, hydrobromic, phosphoric, acetic, fumaric, salicylic, citric, lactic, mandelic, tartaric and methanesulphonic. Such compounds form part of the present invention, as do solvates, for example hydrates, of the compounds of formula (I) or salts thereof.

There is a group of compounds within formula (I) of formula (III):

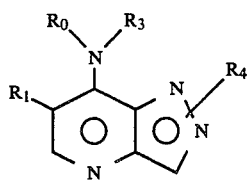
(III)

A further group of compounds within formula (I) is of formula (IV):

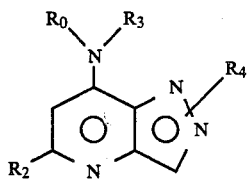
(IV)

A further group of compounds within formula (I) is of formula (V):

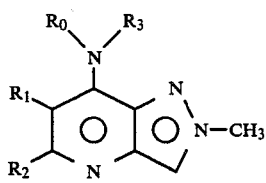
(V)

In formula (III), (IV) and (V) $R_0$, $R_1$, $R_2$, $R_3$ and $R_4$, and suitable and preferred values for these variables, are as described for formula (I).

In a favoured group of compounds within formula (I)
$R_0$ is hydrogen
$R_1$ and $R_2$ are hydrogen,
methyl or ethoxycarbonyl,
$R_3$ is 3-ethoxycarbonylpropyl,
3-(1-(2-oxopyrrolidinyl))propyl,
3-pentanoyloxypropyl, 2-(N-morpholino)ethyl,
2-benzoyloxyethyl, 3-benzylaminocarbonylpropyl,
2-pentanoyloxyethyl, 2-propionyloxyethyl,
3-(n-amylaminocarbonyl)propyl or
3-(iso-amyloxycarbonyl)propyl and $R_4$ is hydrogen or 2-methyl.

The present invention also provides a process for the preparation of a compound of formula (I) or a salt or solvate thereof, which process comprises the reaction of a compound of formula (VI):

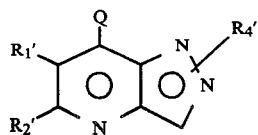
(VI)

wherein Q is a leaving group, $R_1'$, $R_2'$ and $R_4'$ are $R_1$, $R_2$ and $R_4$ or groups or atoms convertible thereto, with a compound of formula (VII):

$HNR_0'R_3'$ (VII)

wherein $R_0'$ and $R_3'$ are $R_0$ and $R_3$ as defined for formula (I) or groups or atoms convertible thereto,
to obtain a compound of formula (Ia)

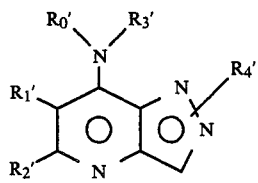
(Ia)

and then performing one or more of the following steps:
(a) when one or more of $R_0'$, $R_1'$, $R_2'$, $R_3'$ or $R_4'$ are not $R_0$, $R_1$, $R_2$, $R_3$ or $R_4$ respectively, converting said one or more substituents to $R_0$, $R_1$, $R_2$, $R_3$, $R_3$ or $R_4$ to obtain a compound of formula (I);

(b) when $R_0'$, $R_1'$, $R_2'$, $R_3'$ and $R_4'$ are $R_0$, $R_1$, $R_2$, $R_3$ and $R_4$, converting one or more of $R_0$, $R_1$, $R_2$, $R_3$ and $R_4$ to another $R_0$, $R_1$, $R_2$, $R_3$ or $R_4$ to obtain a compound of formula (I):

(c) forming a salt and/or solvate of the obtained compound of formula (I).

It will be appreciated that a compound of formula (Ia), or another compound of formula (I), may be converted to compound of formula (I) by interconversion of suitable substituents. Thus certain compounds of formula (I) are useful intermediates in forming other compounds of the present invention.

Salts or solvates e.g. hydrates of the compounds of formula (I) are preferably pharmaceutically acceptable, but those which are not pharmaceutically acceptable may be useful as intermediates in the production of pharmaceutically acceptable salts or solvates. Accordingly such salts or solvates also form part of this invention.

Suitable leaving groups Q include halogens such as chloro and bromo, preferably chloro.

The reaction may be carried out under conventional conditions for nucleophilic aromatic displacements, at normal or elevated temperatures using excess of reagent as solvent or in an inert solvent such as toluene, xylene, ethanol, dimethylformamide, dimethylsulphoxide, dioxan or water. The reaction preferably takes place in a sealed tube or pressure vessel if the compound of formula (VI) is of low boiling point.

Conversiton of an $R_0$ hydrogen to an $R_0$ $C_{1-6}$ alkyl group may be carried out by conventional amine alkylation or acylation (e.g. formylation) followed by reduction.

Conversion of $R_1'/R_2'$ to $R_1/R_2$ may be carried out by conventional functional group interchanges. Thus for example:

(i) a CN group may be provided by the dehydration of an amide group, preferably with phosphorous pentoxide.

(ii) an hydroxymethyl group may be provided by the reduction of an alkoxycarbonyl group, preferably with a metal hydride, such as $LiAlH_4$. In this case it is necessary to protect the pyrazole N-H with a suitable protecting group, such as 2-methoxy-2-propyl.

(iii) an alkanoyl group may be provided by the reaction of a CN group with an organo-metallic reagent such as a Grignard reagent.

(iv) a secondary alcohol group may be provided by the reduction of an alkanoyl group, preferably with a metal hydride.

(v) a tertiary alcohol group may be provided by the reaction of an alkanoyl group with an organo-metallic reagent such as a Grignard reagent.

(vi) a primary aminomethyl group may be provided by the reduction of a CN group, preferably with a metal hydride or using $PtO_2/HCl-H_2$.

(vii) an aminomethyl group may be provided by the reduction of the corresponding amide, preferably with a metal hydride.

(viii) an alkanoyloxyalkyl group may be provided by the acylation of the corresponding alcohol, preferably using the appropriate acid anhydride in trifluoroacetic acid at elevated temperatures.

(ix) an alkanoylaminoalkyl group may be provided by the acylation of the corresponding amino alkyl group, preferably using the appropriate acid anhydride under mild conditions.

(x) a methyl group in particular in the 6-position may be provided by the reduction of an alkoxycarbonyl group, preferably with lithium aluminium hydride.

(xi) an aminoalkyl group may be provided by converting the hydroxy of the corresponding alcohol to a leaving group and reacting with an appropriate amine, preferably a primary or secondary amine.

(xii) alternatively an aminoalkyl group of the formula $CH(R_5)NR_8R_9$ may be provided by the reductive amination of the corresponding keto group $COR_5$, preferably by reaction with the appropriate amine followed by hydrogenation or by reaction with the amine and sodium cyanoborohydride.

(xiii) an alkoxyalkyl group may be provided by the alkylation of the corresponding alcohol, preferably by reaction of the sodium salt of the alcohol with the appropriate alkyl iodide.

(xiv) an alkylthioalkyl group may be provided by the reaction of the corresponding derivatised hydroxyalkyl or haloalkyl group with the appropriate alkylthiol.

An $R_{10}$ hydroxy group in $R_1$ or $R_2$ may be converted to an $R_{10}$ alkoxy group by conventional esterification procedures and an $R_{10}$ hydroxy group may be converted to an $NR_6R_7$ group by condensation with $HNR_6R_7$ in the presence of a dehydrating agent, such as dicyclohexylcarbodiimide.

A $COR_{10}$ group when amide can be converted to a $COR_{10}$ ester group by conventional hydrolysis/esterification in ethanolic HCl. One $COR_{10}$ ester group may be converted to another $COR_{10}$ ester by conventional transesterification procedures. It will be appreciated that when $R_2$ is an ester group, reaction of the compound of formula (VI) with the compound of formula (VII) may also substitute $R_{10}$ in which case subsequent conversion of $R_{10}$ is necessary as described above.

$R_1$ or $R_2$ may be methyl, in which case it may be converted to a $CO_2H$ group by conventional oxidation with an oxidising agent such as potassium permanganate. This conversion is preferably, however, carried out on the intermediate of formula (VI) or at an earlier stage.

To obtain a compound of formula (I) in which $R_1$ is hydrogen when the compound of formula (VII) is a relatively unreactive amine, it is advantageous that $R_1'$ in formula (VI) is alkoxycarbonyl, most preferably ethoxycarbonyl. $R_1'$ alkoxycarbonyl, may then be converted to $R_1$ hydrogen by conventional base hydrolysis followed by decarboxylation Conversions of $R_3/R_3'$ substituents may also be appropriate.

$R_3$ when $-(CH_2)_nCONR_{12}R_{13}$ may be obtained by reaction of an $R_3$ $-(CH_2)_nCO_2R_{11}$ group with the appropriate amine. The $R_3$ $-(CH_2)_nCO_2R_{11}$ group may be prepared directly from a compound of formula (VI) by reaction with $NH_2-(CH_2)_n-CO_2R_{11}$. $R_3$ when

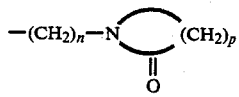

may also be prepared directly from a compound of formula (VI). A compound of formula (Ia) in which $R_3'$ is $-(CH_2)_n-NH_2'$ may be acylated to obtain compounds in which $R_3$ is $-(CH_2)mNHCOR_{14}$ Compounds in which $R_3$ is $-(CH_2)_mOOCR_{14}$ may be prepared by acylation of a compound in which $R_3'$ is $-(CH_2)_m-OH$.

When $R_4$ is hydrogen it may also be acylated during acylation of $R_3$. $R_4$ may be readily deacylated, without affecting $R_3$, by treatment with an alcohol.

Compounds where $R_3$ is $-(CH_2)_nCN$ may serve as intermediates for $R_3$ as $-(CH_2)_{mk}NHCOR_{14}$ by reduction to the corresponding amine followed by acylation. Alternatively partial hydrolysis of the nitriles can give primary amides or more vigorous hydrolysis can lead to acids which can be converted to esters by standard methods.

Compounds where $R_3$ is $-(CH_2)_nCO_2R_{11}$, wherein $R_{11}$ is hydrogen, may serve as intermediates for $R_3$ as $-(CH_2)_nCONR_{12}R_{13}$ or $-(CH_2)_nCO_2R_{11}$, wherein $R_{11}$ is alkyl, by cylisation to the corresponding cyclic amide followed by reaction with the appropriate amine or alcohol.

It will be appreciated that the same cyclic intermediates may serve as protecting groups for $R_3$ $-(CH_2)-nCO_2R_{11}$ during conventional $R_1'/R_2'$ to $R_1/R_2$ functional group interchanges.

An $R_4$ hydrogen atom may be converted to an $R_4$ $C_{1-6}$ alkyl group by conventional alkylation procedures.

It will be appreciated that these conversions may take place in any desired or necessary order. Conversions, in particular those involving amine substitution, may also substitute an $R_4$ hydrogen which therefore may need to be protected using an amine protecting group such as 2-methoxy-2-propyl or para-methoxybenzyl, subsequently removed by heating in the presence of an acid such as trifluoroacetic acid.

Pharmaceutically acceptable salts of the compounds of formula (I) may be formed conventionally by reaction with the appropriate acid. Solvates e.g. hydrates may be formed by crystallization from the appropriate solvent.

Compounds of the formula (VI) are either known compounds or can be prepared by analogy with processes for preparing structurally similar known compounds, such as those disclosed in EP-A-0119774 of Beecham Group plc.

For example, compounds of the formula (VI) wherein Q is chloro may be prepared by the phosphorus oxychloride chlorination of a compound of formula (VIII):

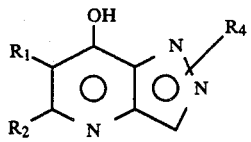

(VIII)

It will be appreciated that the compounds of formula (VIII) wherein $R_4$ is hydrogen exist in the predominant tautomeric form of formula (VIIIa):

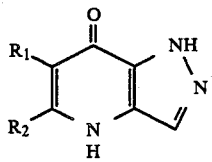

(VIIIa)

Compounds of the formula (VIII) are known compounds or can be prepared by analogy with processes for preparing structurally similar compounds—see for example J. Chem. Soc. Perkin Trans I, 1976 (5), 507.

Those intermediates disclosed herein which are novel compounds form an aspect of this invention, together with the disclosed processes for their preparation.

The compounds of this invention alre indicated as active therapeutic agents by their activity in relevant pharmacological models.

In a further aspect the invention provides a pharmaceutical composition which comprises a compound of formula (I) or a pharmaceutically acceptable salt or solvate thereof and a pharmaceutically acceptable carrier.

The compositions may be adapted for administration via the topical, oral, vaginal rectal or injection routes. The compositions of this invention may be prepared by admixture of the active agent with the carrier and optionally diluents, binder, fillers, disintegrants, flavouring agents, colouring agents, lubricants, preservatives in conventional manner. These conventional excipients may be employed in conventional manner, for example as in the preparation of compositions of ketoprofen, indomethacin, naproxen, acetylsalicylic acid or other anti-inflammatory agents.

The compounds of the invention have topical anti-inflammatory activity and therefore a compound of formula (I) will normally be dispersed in a topically effective vehicle for topical administration to the skin or mucosal membranes.

Cream, lotion, liniment, gel, gel stick, ointment, topical solution, douche, wash, spray, or aerosol formulations that may be used as topical vehicles for compounds of the formula (I) are conventional formulations well known in the art, for example, as described in standard text books of pharmaceutics and cosmetics, such as Harry's Cosmeticology published by Leonard Hill Books, Remington's Pharmaceutical Sciences published by Mack Publishing Co., and the British and U.S. Pharmacopoeias. A standard emulsifying ointment base or glycerol or an hydrous polyethylene glycol are simple examples of suitable vehicles. Aqueous solutions of dispersions may be used as, for example, vaginal douches or washes for mouth or throat.

Examples of oils suitable for inclusion in a standard emulsifying ointment base include mineral oils, vegetable oils, synthetic fatty acid esters, fatty alcohols, lanolin and its derivatives.

These compositions will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

The compositions may also contain anti-oxidants and other conventional ingredients such as preservatives, humectants, perfumes and alcohol. Advantageously, a penetrating agent such as AZONE may also be included.

The compositions for topical treatment may also contain other therapeutic agents such as anti-infective and/or anti-viral agents. Suitable anti-infective agents include the topically applicable antibacterial, anti-yeast, anti-fungal and anti-herpes agents.

These compositions may be used in the topical treatment of atopic, allergic and contact dermatitis, psoriasis, acne, eczema and other inflammatory dermatoses and inflammatory conditions, for example lesions of eyes, ears, nose, throat, vagina and rectum, particularly mucosal membranes. Treatment of inflammation of the skin and mucosal membranes may, however, also be carried out utilising an oral composition of the invention, as hereinbefore described.

It will be appreciated that the amount of compound of the formula (I) used will depend on a number of factors such as the nature and severity of the disorder being treated, and the specific compound being used. A typical formulation will suitably contain 0.1 to 20%, more suitably 0.5 to 5% of the compound of formula (I).

A composition of this invention is useful in the treatment of rheumatism and arthritis and in the treatment of pain and other inflammatory conditions and also in the treatment of the prophylaxis of bronchial asthma, rhinitis, hay fever and allergic eczema. Suitably the oral compositions of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 20 to 3000 mg and more usually in the range 40 to 1000 mg. Alternatively the unit dose may contain from 2-20 mg of active agent and may be administered in multiples if desired to give the preceeding daily dose.

For use in the treatment of prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

No adverse toxicological effects are indicated at any of the aforementioned dosage ranges.

Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A favoured form of oral composition of this invention is a tablet containing the active agent. The active agent may be in the form of a recompressed granulate or the active ingredient in intimate mixture with a lubricant such as magnesium stearate, a filler such as microcrystalline cellulose and a disintegrant such as sodium starch glycollate.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitably for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For parenteral administration, fluid unit dosage forms are prepared utilising a compound of the formula (I) or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The invention further provides a method of treatment or prophylaxis of inflammatory and/or allergic conditions in mammals including man which comprises the administration of a compound of formula (I) or a pharmaceutically acceptable salt or solvate thereof to the sufferer.

The invention also provides a compound of formula (I) or a pharmaceutically acceptable salt or solvate thereof for use as an active therapeutic substance and in particular for use in treating inflammatory and/or allergic conditions in mammals.

Also included in this invention is the use of a compound of formula (I) or a pharmaceutically acceptable salt or solvate thereof for the manufacture of a medicament for the treatment of inflammatory and/or allergic conditions.

Mammals which may be thus treated include humans and domestic or farm animals such as dogs, cats or horses.

Most suitably the medicament will be administered as 1, 2, 3 or 4 doses per day to achieve the daily dose levels previously indicated.

The following Examples illustrate the compounds of the invention and their preparation, the Descriptions illustrate the preparation of intermediates thereto, and the Pharmacological data the biological activity of compounds of the invention.

EXAMPLE 1

Diethyl 7-(3-(1-carboxy)propylamino)-1H-pyrazolo[4,3-b]pyridine-6-carboxylate (E1)

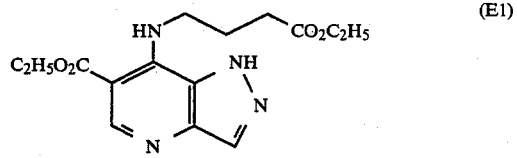

A mixture of ethyl 4-aminobutyrate hydrochloride (2.42 g, 14.4 mmol) and powdered sodium hydroxide (0.58 g, 14.5 mmol) in ethanol (40 ml) was stirred at room temperature for 30 min, then ethyl 7-chloro-1H-pyrazolo[4,3-b]pyridine-6-carboxylate* (1.58 g, 7 mmol) was added and stirring was continued for 40 h. The solvent was evaporated in vacuo and the residual oil was triturated with water to give the title compound (1.66 g, 74%) m.p. 120°–122° C. (ethyl acetate).
*See EP-A-0154220 (Beecham Group plc), Description 5.

δ (CDCl$_3$): 1.35 (6H, m); 2.10 (2H, m); 2.55 (2H, t, J=6 Hz); 3.85 (2H, m); 4.30 (4H, m); 8.20 (1H, s); 8.90 (1H, s); 9.40 (1H, br s).

DESCRIPTION 1

7-(1-(2-Oxopyrrolidinyl))-1H-pyrazolo[4,3-b]pyridine (D1)

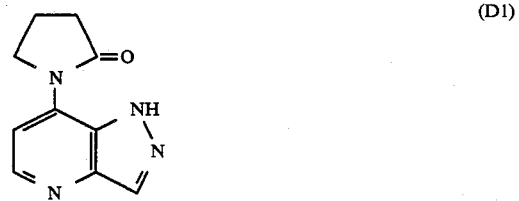

A solution of diethyl 7-(3-(1-carboxy)propylamino)-1H-pyrazolo[4,3-b]pyridine-6-carboxylate (E1) (1.5 g, 4.7 mmol) and sodium hydroxide (750 mg, 18.7 mmol) in water (35 ml) was heated under reflux for 60 min. The solution was cooled and adjusted to pH 6 with 2N hydrochloric acid. The solid was filtered off and washed with water to give 7-(3-(1-carboxy)propylamino)-1H-pyrazolo[4,3-b]pyridine-6-carboxylic acid (1.01 g, 82%), m.p. 246°–249° C. (dec). Without further purification, the diacid was added to near boiling Dowtherm A (50 ml) and the mixture was heated under reflux under nitrogen for 30 min. 60°–80° Petroleum ether (200 ml) was added to the cooled reaction mixture, and the precipitated solid was filtered off and was washed thoroughly with petrol to give the title compound (660 mg, 87%), m.p. 165°–166° C. (ethyl acetate/ethanol).

Found: C, 59.48; H, 4.97; N, 28.02. $C_{10}H_{10}N_4O$ requires C, 59.40; H, 4.98; N, 27.71%.

δ (DMSOd$_6$) 2.2 (2H, m), 2.61 (2H, t, J=8 Hz), 4.02 (2H, t, J=8 Hz), 7.25 (1H, d, J=6 Hz), 8.30 (1H, s), 8.48 (1H, d, J=6 Hz), 12.75 (1H, s).

EXAMPLE 2

Ethyl 4-(7-(1H-Pyrazolo[4,3-b]pyridyl)amino)butanoate (E2)

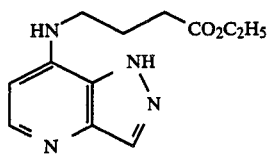

A solution of 7-(1-(2-oxopyrrolidinyl))-1H-pyrazolo-[4,3-b]pyridine (D1) (550 mg, 2.7 mmol) and sodium hydroxide (0.33 g, 8 mmol) in water (20 ml) was heated under reflux for 2 h. The solution was cooled and adjusted to pH 6 with 2N hydrochloric acid. The precipitated solid was washed with water and dried to give 4-(7-(1H-pyrazolo[4,3-b]pyridyl)amino)butanoic acid (540 mg, 90%), m.p. 228°–238° C. (dec). Without further purification, the acid was suspended in ethanolic hydrogen chloride (20 ml) and stirred at room temperature for 3 days. The solvent was evaporated in vacuo to leave a yellow solid which was dissolved in water (25 ml). The solution was adjusted to pH 9 with 10% sodium carbonate solution, and was extracted with ethyl acetate. The extracts were washed with brine, dried (MgSO$_4$) and evaporated in vacuo to leave an oil which slowly solidified. The crude solid was recrystallised from ethyl acetate to give the title compound (360 mg, 59%), m.p. 129°131° C.

Found: C, 57.74; H, 6.46; N, 22.79. $C_{12}H_{16}N_4O_2$ requires C, 58.05; H, 6.50; N, 22.57%.

δ (CDCl$_3$): 1.20 (3H, t, J=8 Hz), 1.90 (2H, m), 2.35 (2H, t, J=7 Hz), 3.35 (2H, m), 4.10 (2H, q, J=8 Hz), 6.35 (1H, d, J=6 Hz), 6.45 (1H, br s), 8.10 (1H, s), 8.30 (1H, d, J=6 Hz), 12.10 (1H, br s).

EXAMPLE 3

5-Methyl-7-(3-(1-(2-oxopyrrolidinyl))propylamino)-1H-pyrazolo[4,3-b]pyridine (E3)

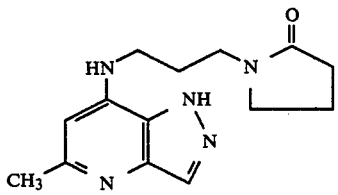

A solution of 7-chloro-5-methyl-1H-pyrazolo[4,3-b]pyridine* (1.5 g, 8.95 mmol) and 1-(3-aminopropyl)-2-oxo-pyrrolidine (2.5 ml, 17.8 mmol) in dry xylene (15 ml) was heated under reflux for 3 days. The supernatant solution was decanted and the oil was dissolved in ethanol and acidified with ethanolic hydrogen chloride. After removing the solvent in vacuo, the residue was crystallised from ethanol/ethyl acetate. The solid was dissolved in a little water and the solution was adjusted to pH 8 with 10% sodium carbonate solution, then saturated with sodium chloride and extracted with ethyl acetate. The extracts were dried (MgSO$_4$) and evaporated in vacuo and the residue was recrystallised from ethanol/ethyl acetate/petrol to give the title compound, m.p. 183°–187° C.
*See EP-A-119774 (Beecham Group plc) Description 1(d).

δ (DMSOd$_6$) 1.7–2.0 (4H, m), 2.25 (2H, t, J=7 Hz), 2.40 (3H, s), 3.2–3.5 (6H, m), 6.2 (1H, s), 6.35 (1H, br s), 7.9 (1H, s), 12.5 (1H, br s).

EXAMPLE 4

7-[3-Pentanoyloxypropylamino]-5-methyl-1H-pyrazolo[4,3-b]pyridine (E4)

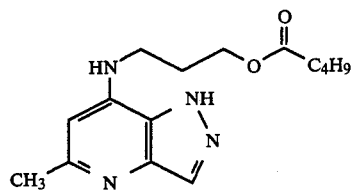

7-[3-Hydroxypropylamino]-5-methyl-1H-pyrazolo[4,3-b]-pyridine,* (0.15 g, 0.73 mmol) was suspended in dry pyridine (2 ml) and 1,4-dioxan (2 ml) and cooled in an ice-bath. A solution of valeryl chloride (0.18 ml, 2.1 equiv.) in dioxan (1.5 ml) was added dropwise with stirring and then left at room temperature overnight. Methanol (10 ml) was added and the resulting solution stirred for 1 h and then solvents removed under reduced pressure. The residue was chromatographed on basic alumina eluting initially with ethyl acetate rising to 30% methanol/ethyl acetate. After removal of solvent a colourless oil was obtained, which on trituration with ether gave the title compound as a white solid, m.p. 92°–95° C.
*See EP-A-0152910 (Beecham Group plc), Example 2.

δ (MeOH-d$_4$) TMS in CDCl$_3$ as external standard 0.6–2.6 (11H, m), 2.47 (3H, s), 3.36 (2H, t, J=6 Hz), 4.14 (2H, t, J=6 Hz), 6.19 (1H, s), 7.87 (1H, s).

Found: C, 61.92; H, 7.69; N, 19.16 $C_{15}H_{22}N_4O_2$ requires C, 62.05; H, 7.64; N, 19.30%.

EXAMPLE 5

7-[2-(N-Morpholino)ethylamino]-5-methyl-1H-pyrazolo [4,3-b]pyridine dihydrate (E5)

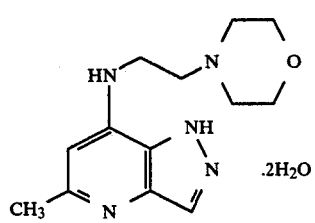

A mixture of 7-chloro-5-methyl-1H-pyrazolo[4,3-b]-pyridine (1.5 g), 2-N-morpholinoethylamine (3.5 g) in xylene (55 ml) was heated at reflux under nitrogen for 2 days. After allowing to cool, solvent was removed under reduced pressure to leave a brown gum, which after neutralisation (1 equivalent of 10% NaOH added to aqueous methanol solution and solvents removed) was purified by chromatography on basic alumina with initially ethyl acetate as eluant (% of MeOH slowly increased to 25%). As analysis indicated a small proportion of chlorine was present the product was redissolved in water/methanol, treated with a further quantity of 10% sodium hydroxide and left to crystallise at 4° C. The resulting pale yellow crystals (0.363 g, 16%) of the title compound were collected washed with water and dried under vacuum, m.p. softening at 85° then melting at 225°–226° C.

Found: C, 52.36; H, 7.81; N, 23.66. $C_{13}H_{19}N_5O.2H_2O$ requires C, 52.50; H, 7.79; N, 23.55%.

$\delta$ ($CD_3OD$) 2.49 (3H, s), 2.55 (4H, br t), 2.72 (2H, t, J=6.5 Hz), 3.47 (2H, t, J=6.5 Hz), 3.72 (4H, t, J=5 Hz)

EXAMPLE 6

7-[3-Acetoxypropylamino]-5-methyl-1H-pyrazolo[4,3-b]-pyridine (E6)

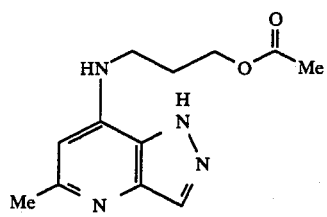

(E6)

The title compound was prepared from 7(3-hydroxypropylamino)-5-methyl-1H-pyrazolo[4,3-b]pyridine (1.125 g) and acetyl chloride by the general method of Example 4 with the following addition. After removal of solvents under reduced pressure the crude reaction mixture was dissolved in water and brought to pH 9 with 10% sodium hydroxide. The resulting solid was collected and dried before purifying by column chromatography under the conditions used for Example 4. A clear gum was obtained which on trituration with ether gave the title compound as a white solid, m.p. 115°–119° C.

Found: C, 58.23; H, 6.67; N, 22.65. $C_{12}H_{16}N_4O_2$ requires C, 58.05; H, 6.50; N, 22.57%.

$\delta$ ($DMSO-d_6$) 1.9–2.1 (m, 2H), 2.02 (s, 3H), 2.49 (s, 3H), 3.45 (q, 2H), 4.15 (t, 2H), 6.40 (s, 1H), 7.98 (brs, 1H), 8.07 (s, 1H), 13.6 (brs, 1H).

EXAMPLE 7

7-[2-Benzoyloxyethylamino]-5-methyl-1H-pyrazolo[4,3-b]pyridine (E7)

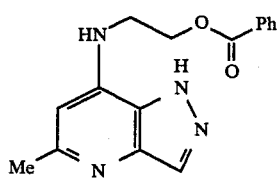

(E7)

The title compound was prepared from 7-(2-hydroxyethyl-amino)-5-methyl-1H-pyrazolo[4,3-b]pyridine (2 g) and benzoyl chloride by the general method of Example 4 without the addition of methanol. The crude reaction mixture was poured into a large excess of water and extracted with ethyl acetate (×3). The combined organic layers were washed with water (×2), dried with anhydrous sodium sulphate, filtered and evaporated to dryness. The resulting intermediate dibenzoylated compound was recrystallized from carbon tetrachloride/60°–80° C. petrol to give a pale yellow solid, m.p. 136°–138° C.

Found: C, 68.75; H, 5.06; N, 13.89. $C_{23}H_{20}N_4O_3$ requires C, 68.99; H, 5.03; N, 13.99%. The recrystallized dibenzoyl compound (1.91 g) was suspended in methanol (25 ml) and stirred at room temperature for 22 h. Solvent was removed under reduced pressure and the residue crystallized from ether/pentane. The title compound was obtained as a pale yellow solid, m.p. 168°–170°.

Found: C, 64.70; H, 4.94; N, 18.82. $C_{16}H_{16}N_4O_2$ requires C, 64.85; H, 5.44; N, 18.91%. Found M+ 296.1273. $C_{16}H_{16}N_4O_2$ requires 296.1273.

$\delta$ ($DMSO-d_6$) 2.40 (s, 3H), 3.71 (q, 2H), 4.51 (t, 2H), 6.40 (s, 1H), 6.6 (brs, 1H), 7.46–7.58 (m, 2H), 7.61–7.72 (m, 1H), 7.90 (s, 1H), 7.94–8.02 (m, 2H), 12.50 (brs, 1H).

EXAMPLE 8

(7-(1H-Pyrazolo[4,3,-b]pyridyl)amino)butanoic acid benzylamide (E8)

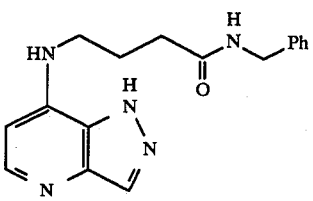

(E8)

A solution of 7-(1-(2-oxopyrrolidinyl)-1H-pyrazolo[4,3-b]pyridine (D1) (400 mg) and benzylamine (5 ml) in dry xylene (15 ml) was heated under reflux for 2 weeks. The solvent was evaporated in vacuo and the resulting oil was purified by column chromatography on alumina eluting with 2% methanol/chloroform. The solid obtained was recrystallized from ether/methanol to give the title compound as a white solid (292 mg), m.p. 144°–145° C.

Found: C, 65.80; H, 6.38; N, 22.16. $C_{17}H_{19}N_5O$ requires C, 66.00; H, 6.19; N, 22.64%. Found M+ 309.1589. $C_{17}H_{19}N_5O$ requires 309.1593.

$\delta$ ($DMSO-d_6$) 1.90 (q, 2H), 2.30 (t, 2H), 3.27 (t, 2H), 4.25 (d, 2H), 6.31 (d, 1H), 6.50 (t, 1H), 7.15–7.30 (m, 5H), 8.02 (s, 1H), 8.10 (d, 1H), 8.54 (t, 1H), 12.60 (brs, 1H).

EXAMPLE 9

7-(2-Pentanoyloxyethylamino)-5-methyl-1H-pyrazolo[4,3-b]pyridine (E9)

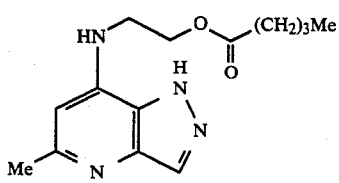

(E9)

The title compound was prepared from 7-(2-hydroxyethylamino)-5-methyl-1H-pyrazolo[4,3-b]pyridine* (2.5 g) and valeryl chloride by the general method of Example 4. The product obtained was purified by column chromatography as described for Example 4 and then partitioned between ethyl acetate and water, the aqueous layer being brought to pH 9 with 10% sodium hydroxide. The ethyl acetate layer was separated and the aqueous layer extracted with ethyl acetate (×3). The combined organic layers were dried (anhydrous sodium sulphate) and evaporated to dryness to give a pale yellow gum which on trituration with ether and washing the resulting solid with ethyl acetate/ether gave the title compound as a pale yellow solid (1.48 g, 41%), m.p. 117°–119°.

*See EP-A-0152910 (Beecham Group plc), Example 3.

Found: C, 60.61; H, 7.17; N, 20.59. C₁₄H₂₀N₄O₂ requires C, 60.85; H, 7.30; N, 20.27%. Found M+ 276.1586. C₁₄H₂₀N₄O₂ requires 276.1586.

δ (CDCl₃) 0.85 (t, 3H), 1.0–1.75 (m, 4H), 2.2 (t, 2H), 2.6 (s, 3H), 3.58 (brt, 2H), 4.30 (t, 2H), 6.25 (s, 1H), 7.97 (s, 1H), 8.00 (brs, 1H).

EXAMPLE 10

7-[2-Propionyloxyethylamino]-5-methyl-1H-pyrazolo[4,3-b]pyridine (E10)

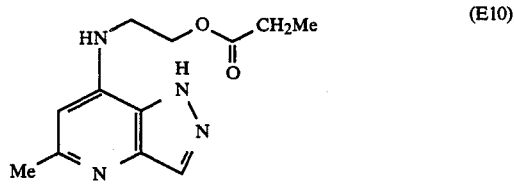

The title compound was prepared from 7-(2-hydroxyethylamino)-5-methyl-1H-pyrazolo[4,3-b]pyridine (2 g) and propionyl chloride by the method of Example 4. After purification by column chromatography on basic alumina with ethyl acetate and then a rising percentage of methanol as eluant the title compound was obtained as a white solid (1.7 g, 66%), m.p. 187°–190° C.

Found: C, 58.18; H, 6.60; N, 22.51. C₁₂H₁₆N₄O₂ requires C, 58.05; H, 6.50; N, 22.57%. Found M+ 248.1272. C₁₂H₁₆N₄O₂ requires 248.1273.

δ (CDCl₃+DMSO-d₆) 1.12 (t, 3H), 2.37 (q, 2H), 2.53 (s, 3H), 3.4–3.8 (m, 2H), 4.35 (t, 2H), 6.25 (s, 1H), 6.35 (brm, 1H), 7.90 (s, 1H), 12.35 (brs, 1H).

EXAMPLE 11

(7-(1H-Pyrazolo[4,3-b]pyridyl)amino)butanoic acid amylamide (E11)

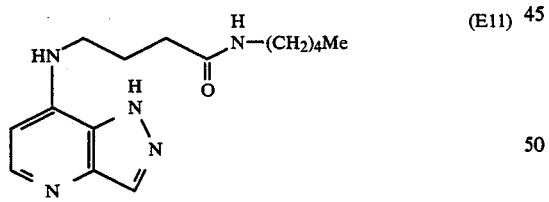

A solution of ethyl 4-(7-(1H-pyrazolo[4,3-b]pyridyl)amino) butanoate (E1) (250 mg) and n-amylamine (5 ml) in dry xylene (5 ml) was heated under reflux for 5 h. The solution was cooled and the resulting white solid collected, washed with pentane and recrystallized from ether/methanol to give the title compound (140 mg), m.p. 183°–184° C.

Found: C, 62.23; H, 8.22; N, 23.77. C₁₅H₂₃N₅O requires C, 62.26; H, 8.01; N, 24.19%. Found M+ 289.1899. C₁₅H₂₃N₅O requires 289.1902.

δ (DMSO-d₆) 0.85 (t, 3H), 1.1–1.5 (m, 6H), 1.87 (dd, 2H), 2.25 (t, 2H), 3.05 (dd, 2H), 3.3 (dd, 2H), 6.3 (d, 1H), 6.52 (t, 1H), 7.82 (t, 1H), 8.01 (s, 1H), 8.10 (d, 1H), 12.6 (brs, 1H).

EXAMPLE 12

Isoamyl (7-(1H-pyrazolo[4,3-b]pyridyl)amino)butanoate (E12)

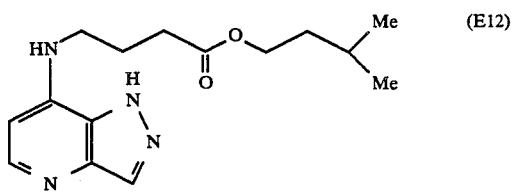

A solution of 4-(7-(1H-pyrazolo[4,3-b]pyridyl)amino)butanoic acid (500 mg) prepared by the method given in E2 and isoamyl alcohol (2 ml) in dry xylene (10 ml) with a drop of concentrated hydro-chloric acid as catalyst was heated under reflux for 2 h. The solution was cooled and the solvent evaporated in vacuo. The residue was dissolved in methanol/water, adjusted to pH 9 with 10% sodium carbonate solution, then extracted with ethyl acetate (3×50 ml) dried (MgSO₄) and evaporated to dryness in vacuo to leave a pale yellow oil which slowly solidified. The solid was recrystallized from ether-methanol to give the title compound (200 mg) as a white crystalline solid, m.p. 98°–101° C.

Found: C, 61.93; H, 7.88; N, 19.32. C₁₅H₂₂N₄O₂ requires C, 62.05; H, 7.64; N, 19.30%. Found: M+ 290.1746. C₁₅H₂₂N₄O₂ requires 290.1743.

δ (DMSO-d₆) 0.85 (d, 6H), 1.35 (dd, 2H), 1.52–1.70 (m, 1H), 1.90 (q, 2H), 3.45 (q, 2H), 4.06 (t, 2H), 6.34 (d, 1H), 6.55 (brs, 1H), 8.01 (s, 1H), 8.09 (d, 1H), 12.65 (brs, 1H).

DESCRIPTION 2

7-(2-Hydroxyethylamino)-2,5-dimethylpyrazolo[4,3-b]pyridine (D2)

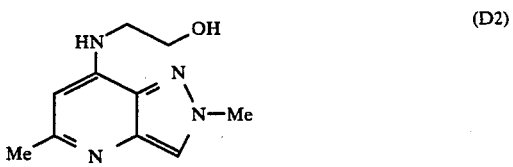

7-Chloro-2,5-dimethylpyrazolo[4,3-b]pyridine* (1.49 g) and ethanolamine (2 ml) in dry xylene (10 ml) were heated under reflux for 12 h. The solvent was removed under reduced pressure and the residue dissolved in methanol/water (5 ml) and basified to pH 9 with 10% sodium carbonate solution to give a sticky gum. This was extracted into ethyl acetate, dried, and evaporated to dryness to give a yellow oil. This was chromatographed on basic alumina eluting with 10% methanol/ethyl acetate to give the title compound as a white solid (570 mg) m.p. 163°–165° C.

*See EP-A-0152910 (Beecham Group plc), Description 2.

Found: M+ 206.1177. C₁₀H₁₄N₄O requires 206.1168.

δ (CDCl₃) 2.50 (s, 3H), 3.48 (q, 2H), 3.94 (t, 2H), 4.09 (s, 3H), 5.65 (brs, 1H), 6.05 (s, 1H), 7.83 (s, 1H).

EXAMPLE 13

7-(2-Pentanoyloxyethylamino)-2,5-dimethyl-pyrazolo[4,3-b]pyridine (E13)

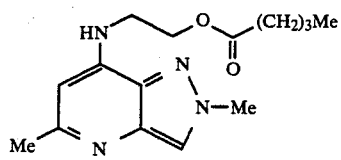 (E13)

The title compound was prepared from 7-(2-hydroxyethylamino)-2,5-dimethylpyrazolo[4,3-b]pyridine (D2) (400 mg) and valeryl chloride by the general method of Example 4. The solid obtained was recrystallized from ether/methanol to give the title compound (300 mg, 74%), m.p. 78°–80° C.

Found: C, 61.77; H, 7.75; N, 19.20. $C_{15}H_{22}N_4O_2$ requires C, 62.05; H, 7.75; N, 19.30%. Found M+ 290.1743. $C_{15}H_{22}N_4O_2$ requires 290.1743.

δ (CDCl$_3$) 0.90 (t, 3H), 1.28–1.40 (m, 2H), 1.56–1.68 (m, 2H), 2.35 (t, 2H), 2.57 (s, 3H), 3.63 (q, 2H), 4.17 (s, 3H), 4.38 (t, 2H), 5.50 (t, 1H), 6.15 (s, 1H), 7.98 (s, 1H).

MOUSE CANTHARIDIN TEST

Compounds were tested for topical anti-inflammatory activity in a cantharidin mouse ear screen, modified from Swingle, Reiter and Schwartzmiller [Arch. int. Pharmacodyn. 254, 168–176, 1981].

25 μg cantharidin (in 10 μl tetrahydrofuran:methanol, 1:1 v/v) is applied to both ears of CD1 male mice, 25 g bodyweight. 8 animals are used per experimental group. Compounds are included in the irritant solution applied to the left ear only. Negative control animals receive no treatment except 10 μl solvent on each ear. After 24 hours, the animals are killed and the ears are removed by cutting along the hairline and then weighed. The swelling induced by cantharidin is assessed as the increase in the weight of the right ears over that of the right ears of solvent-treated control animals, as a proportion of the weight of solvent-treated right ears. The swelling induced in the same animals in the presence of test compound is similarly the increase in the weight of the left ears over that of the left ears of the solvent-treated control animals, expressed as a proportion of the weight of solvent-treated left ears. This value is expressed as % of the full (right ear) swelling, and hence a % inhibition by the test compound is calculated:

thus, % inhibition=([means wt.left experimental ears−mean wt.left 100−control ears]/[mean wt.left control ears])×100 ([mean wt.right experimental ears−mean wt.right control ears]/[mean wt.right control ears])

This method reduces the contribution of inter-animal variations in responsiveness to the inflammatory stimulus, and also compensates for any consistent bias in cutting off left and right ears. The significance of the inhibition is calculated using a paired 't' test of the two values of proportional weight increases.

| Compound Example Number | Dose (μg/ear) | % Inhibition |
|---|---|---|
| 2 | 500 | 94.6*** |
| 3 | 200 | 75.3*** |
| 4 | 200 | 69.9*** |
| 5 | 200 | 97.6*** |
| 6 | 200 | 70*** |
| 7 | 500 | 99.6*** |
| 8 | 500 | 95*** |
| 9 | 200 | 69*** |
| 10 | 200 | 55** |
| 12 | 200 | 78*** |

**$p < 0.01$;
***$p < 0.001$.
Student's 't' test.

MOUSE OXAZOLONE TEST

Compounds were tested for topical anti-inflammatory activity in a model system using the mouse sensitised to oxazolone, by a method modified from that of Dietrich and Hess [Int. Arch. Allergy, 38, 246 (1970)].

Mice are sensitised with oxazolone (2 mg in 20 μl acetone) on a shaved area of the abdomen. CD1 male mice of around 25 g bodyweight (8 animals per group) are used. 5 days later, the animals receive 10 μl tetrahydrofuran:methanol (1:1 v/v) on the right ear and the test compound in 10 μl of the same solvent on the left ear. 1 hour later, the animals are challenged with 100 μg oxazolone in 10 μl acetone on each ear. Negative control animals receive no treatment except 10 μl tetrahydrofuran:methanol at the initial time point. After 24 hours, the animals are killed and the ears are removed by cutting along the hairline and then weighed. The swelling induced by oxazolone is assessed as the increase in the weight of the right ears over that of the right ears of solvent-treated control animals, as a proportion of the weight of solvent-treated right ears. The swelling induced in the same animals in the presence of test compound is similarly the increase in the weight of the left ears over that of the left ears of the solvent-treated control animals, expressed as a proportion of the weight of solvent-treated left ears. This value is expressed as % of the full (right ear) swelling, and hence a % inhibition by the test compound is calculated:

thus, % inhibition=([mean wt.left experimental ears−mean wt.left 100−control ears]/[mean wt.left control ears])×100 ([mean wt.right experimental ears−mean wt.right control ears]/[mean wt.right control ears])

This method reduces the contribution of inter-animal variations in responsiveness to the inflammatory stimulus, and also compensates for any consistent bias in cutting off left and right ears. The significance of the inhibition is calculated using a paired 't' test of the two values of proportional weight increases.

| Compound Example Number | Dose (μg/ear) | % Inhibition |
|---|---|---|
| 2 | 200 | 48.6*** |
| 3 | 200 | 44.1* |
| 5 | 200 | 61.6* |
| 6 | 200 | 53*** |
| 7 | 200 | 30** |

*$p < 0.1$;
**$p < 0.01$;
***$p < 0.001$.
Student's 't' test.

We claim:

1. A compound of the formula (1) or a pharmaceutically acceptable salt or solvate thereof:

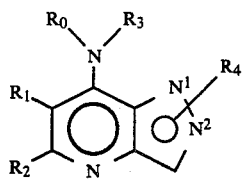

in which:

R$_0$ is hydrogen or C$_{1-6}$ alkyl;

R$_1$ and R$_2$ are both hydrogen; or

R$_1$ is hydrogen, C$_{1-6}$ alkyl; and R$_2$ is CN; CR$_5$R$_6$Y where R$_5$ and R$_6$ are independently selected from hydrogen and C$_{1-4}$ alkyl and Y is selected from hydrogen, OR$_7$ or SR$_7$ where R$_7$ is hydrogen, C$_{1-6}$ alkyl or C$_{2-4}$ alkanoyl, and NR$_8$R$_9$ and R$_9$ are independently hydrogen, C$_{1-4}$ alkyl, C$_{2-4}$ alkenyl or C$_{2-4}$ alkanoyl or together are C$_{4-6}$ polymethylene; or COR$_{10}$ where R$_{10}$ is OH or C$_{1-4}$ alkyl, C$_{1-6}$ alkoxy, C$_{2-6}$ alkenyloxy, phenoxy or benzyloxy where the phenyl/benzyl ring is optionally substituted by one or two of halogen, CF$_3$, C$_{1-4}$ alkoxy and C$_{1-4}$ alkyl; or R$_{10}$ is NR$_{20}$R$_{21}$ where R$_{20}$ and R$_{21}$ are independently hydrogen, C$_{1-6}$ alkyl, C$_{2-6}$ alkenyl, benzyl or phenyl optionally substituted as described above; or R$_2$ is hydrogen, C$_{1-6}$ alkyl, or phenyl optionally substituted by halogen, CF$_3$, C$_{1-4}$ alkoxy or C$_{1-4}$ alkyl; and R$_1$ is CN, CR$_5$R$_6$Y or COR$_{10}$ as defined for R$_2$ above; or R$_1$ and R$_2$ together form C$_3$-C$_6$ polymethylene optionally substituted by C$_1$-C$_4$ alkyl;

R$_3$ is —(CH$_2$)$_n$CO$_2$R$_{11}$, —(CH$_2$)$_n$CONR$_{12}$R$_{13}$, —(CH$_2$)$_n$CN,

—(CH$_2$)$_m$—O—C—R$_{14}$
          ‖
          O

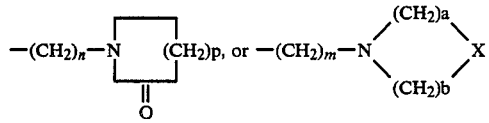

where a, b, n, m and p are integers and n is 1 to 10, m is 2 to 10, p is 3 to 5, a is 1 to 3, and b is 1 to 3, and R$_{11}$ is hydrogen, C$_{1-8}$ alkyl, benzyl or phenyl, R$_{12}$ and R$_{13}$ are independently hydrogen, C$_{1-6}$ alkyl, benzyl or phenyl, or together form C$_{3-8}$ alkylene, R$_{14}$ is C$_{1-4}$ alkyl, benzyl or phenyl and X is oxygen, sulphur, NH or N—C$_{1-4}$ alkyl, and R$_4$ is hydrogen; or C$_{1-4}$ alkyl or benzyl optionally substituted in the phenyl ring by one or two of halogen, CF$_3$, C$_{1-4}$ alkoxy or C$_{1-4}$ alkyl, and is attached at nitrogen atom 1 or 2.

2. A compound according to claim 1 wherein Ro is selected from the group consisting of hydrogen, methyl, ethyl, n- or iso-propyl; R$_1$ and R$_2$ are selected from the group consisting of hydrogen, methyl, aminomethyl, N-substituted aminomethyl and acetamidomethyl, or COR$_{10}$ where R$_{10}$ is as defined in claim 1, or R$_1$ and R$_2$ together form C$_3$ or C$_4$ polymethylene; R$_3$ is selected from the group consisting of 3-ethoxycarbonylpropyl, 3-(1-(2-oxopyrrolidinyl))-propyl, 3-pentanoyloxypropyl, 2-(N-morpholino)ethyl, 3-acetoxypropyl, 2-benzoyloxyethyl, 3-benzylaminocarbonylpropyl, 2-pentanoyloxyethyl, 2-propionyloxyethyl, 3-(n-amylaminocarbonyl)propyl and 3-(isoamyloxycarbonyl)propyl, and R$_4$ is selected from the group consisting of hydrogen, methyl, ethyl, n- and iso-propyl and benzyl.

3. A compound according to claim 1 wherein R$_o$ is hydrogen, R$_1$ and R$_2$ are selected from the group consisting of hydrogen, methyl or ethoxycarbonyl, R$_4$ is hydrogen or 2-methyl and R$_3$ is selected from the group consisting of 3-ethoxycarbonylpropyl, 3-(1-(2-oxopyrrolidinyl))-propyl, 3-pentanoyloxy-propyl, 2-(N-morpholino)ethyl, 3-acetoxypropyl, 2-benzoyloxyethyl, 3-benzylaminocarbonylpropyl, 2-pentanoyloxyethyl, 2-propionyloxyethyl, 3-(n-amylaminocarbonyl)propyl and 3-(iso-amyloxycarbonyl)propyl.

4. A compound according to claim 1 of formula (III):

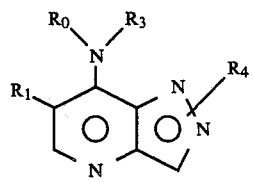

wherein R$_o$, R$_1$, R$_3$ and R$_4$ are as defined in claim 1.

5. A compound according to claim 1 of formula (IV):

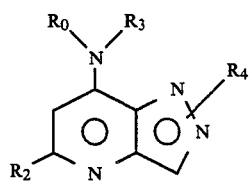

wherein R$_o$, R$_2$, R$_3$ and R$_4$ are as defined in claim 1.

6. A compound according to claim 1 of formula (V):

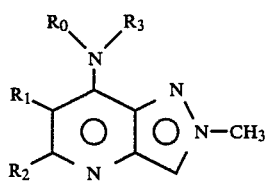

wherein R$_0$, R$_1$, R$_2$ and R$_3$ are as defined in claim 1.

7. A compound according to claim 1 which is selected from the group consisting of:

Diethyl 7-(3-(1-carboxy)propylamino)-1H-pyrazolo-[4,3-b]pyridine-6-carboxylate,

Ethyl 4-(7-(1H-pyrazolo[4,3-b]pyridyl)amino)-butanoate,

5-Methyl-7-(3-(1-(2-oxopyrrolidinyl))propylamino)-1H-pyrazolo[4,3-b]pyridine,

7-[3-Pentanoyloxopropylamino]-5-methyl-1H-pyrazolo-[4,3-b]pyridine,

7-[2-(N-Morpholino)ethylamino]-5-methyl-1H-pyrazolo-[4,3,-b]pyridine dihydrate,

7-[3-Acetoxypropylamino]-5-methyl-1H-pyrazolo-[4,3-b]-pyridine,

7-[2-Benzoyloxyethylamino]-5-methyl-1H-pyrazolo-[4,3-b]pyridine, (7-(1H-Pyrazolo[4,3-b]pyridyl)amino)butanoic acid benzylamide,
7-[2-Pentanoyloxyethylamino]-5-methyl-1H-pyrazolo-[4,3-b]pyridine,
7-[2-Propionyloxyethylamino]-5-methyl-1H-pyrazolo-[4,3-b]pyridine,
(7-(1H-Pyrazolo[4,3-b]pyridyl)amino)butanoic acid amylamide,
Isoamyl (7-(1H-pyrazolo[4,3-b]pyridyl)amino)-butanoate or
7-[2-Pentanoyloxyethylamino]-2,5-dimethyl-pyrazolo-[4,3-b]pyridine.

8. A pharmaceutical composition for use in treating inflammatory and/or allergic disorders comprising an effective amount of a compound according to claim 1 and a pharmaceutically acceptable carrier.

9. A method of treating inflammatory and/or allergic disorders in mammals which comprises administering an effective amount of a compound according to claim 1, or a pharmaceutically acceptable salt or solvate thereof, to a sufferer.

* * * * *

UNITED STATES PATENT AND TRADEMARK OFFICE
CERTIFICATE OF CORRECTION

PATENT NO. : 4,818,754
DATED : April 4, 1989
INVENTOR(S) : Robert W. Ward et al.

It is certified that error appears in the above-identified patent and that said Letters Patent is hereby corrected as shown below:

In the Title, "[4,3-B]" should be -- [4,3-b] --.

In the Abstract, under the definition of $R_1$, after "$COR_{10}$" should be inserted -- where $R_{10}$ --.

under the definition of $R_3$,

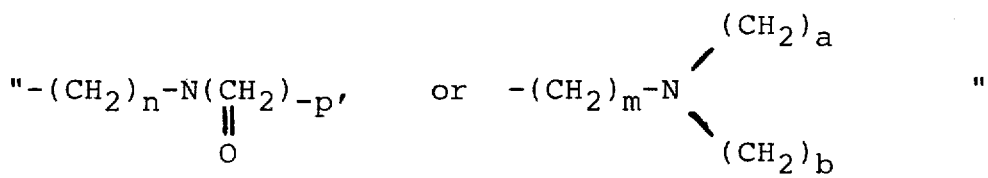

should be

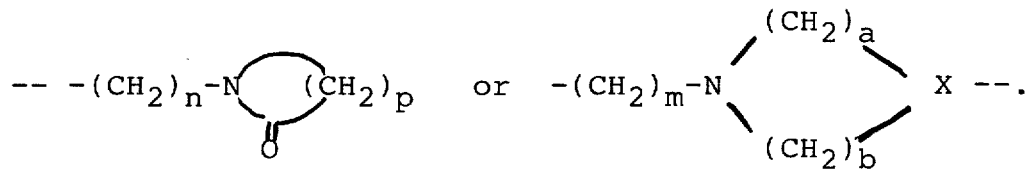

UNITED STATES PATENT AND TRADEMARK OFFICE
CERTIFICATE OF CORRECTION

PATENT NO. : 4,818,754
DATED : April 4, 1989
INVENTOR(S) : Robert W. Ward et al.

It is certified that error appears in the above-identified patent and that said Letters Patent is hereby corrected as shown below:

Column 1, line 2, "[4,3-B]" should be -- [4,3-b] --.

Column 2, line 47, "amlaminocarbonyl)propyl" should be

-- amylaminocarbonyl)propyl --.

Column 6, line 40, "$-(CH_2)_{mk}NHCOR_{14}$" should be

-- $-(CH_2)_m NHCOR_{14}$ --.

Column 8, lines 49 and 65, "treatment of the prophylaxis"

should be -- treatment or prophylaxis --.

Column 17, lines 51-55 and column 18, lines 43-47, "([means wt.left experimental ears-mean wt.left 100-control ears]/[mean wt. left control ears]) x 100 ([mean wt.right experimental ears-mean wt.right control ears]/[mean wt.right control ears])" should be -- [100-[(mean wt. left experimental ears - mean wt. left control ears]/[mean wt. left control ears]); ([mean wt. right experimental ears - mean wt. right control ears]/mean wt. right control ears])]]x100 --.

UNITED STATES PATENT AND TRADEMARK OFFICE
CERTIFICATE OF CORRECTION

PATENT NO. : 4,818,754
DATED : April 4, 1989
INVENTOR(S) : Robert W. Ward et al.

It is certified that error appears in the above-identified patent and that said Letters Patent is hereby corrected as shown below:

Claim 7, column 20, line 57, "Ethyl    4-" should be
-- Ethyl 4- --.

Claim 7, column 21, line 11, "Isoamyl    (7-" should be
-- Isoamyl (7- --.

Signed and Sealed this

Second Day of January, 1990

Attest:

JEFFREY M. SAMUELS

Attesting Officer    Acting Commissioner of Patents and Trademarks